(12) United States Patent
Nair et al.

(10) Patent No.: US 7,888,375 B2
(45) Date of Patent: Feb. 15, 2011

(54) PYRIDINONE DIKETO ACIDS: INHIBITORS OF HIV REPLICATION

(75) Inventors: Vasu Nair, Athens, GA (US); Byung I. Seo, Athens, GA (US); Vinod R. Uchil, Athens, GA (US)

(73) Assignee: The University of Georgia Research Foundation, Inc, Athens, GA (US)

( * ) Notice: Subject to any disclaimer, the term of this patent is extended or adjusted under 35 U.S.C. 154(b) by 752 days.

(21) Appl. No.: 11/827,959

(22) Filed: Jul. 13, 2007

(65) Prior Publication Data

US 2008/0020010 A1  Jan. 24, 2008

Related U.S. Application Data

(60) Provisional application No. 60/831,990, filed on Jul. 19, 2006, provisional application No. 60/920,196, filed on Mar. 27, 2007, provisional application No. 60/920,197, filed on Mar. 27, 2007.

(51) Int. Cl.
*A61K 31/44* (2006.01)
*C07D 211/86* (2006.01)
(52) U.S. Cl. .................. 514/354; 546/298; 514/355
(58) Field of Classification Search .................. None
See application file for complete search history.

(56) References Cited

U.S. PATENT DOCUMENTS

| 6,492,423 | B1 | 12/2002 | Sergio et al. |
| 6,620,841 | B1 | 9/2003 | Fujishita et al. |
| 2003/0171406 | A1 | 9/2003 | Sato |
| 2005/0239819 | A1 | 10/2005 | Satoh et al. |
| 2005/0245530 | A1 | 11/2005 | Borzilleri et al. |
| 2005/0261322 | A1 | 11/2005 | Naidu et al. |
| 2005/0267105 | A1 | 12/2005 | Naidu et al. |
| 2006/0084665 | A1 | 4/2006 | Satoh et al. |
| 2006/0199956 | A1 | 9/2006 | Naidu et al. |
| 2007/0249687 | A1 | 10/2007 | Yoshida |

FOREIGN PATENT DOCUMENTS

| GB | 1291571 A | 10/1972 |
| WO | 9962520 | 12/1999 |
| WO | WO 9962513 | 12/1999 |
| WO | WO 9962897 | 12/1999 |
| WO | WO0039086 | 7/2000 |
| WO | WO0100578 A1 | 1/2001 |
| WO | WO0196329 A1 | 12/2001 |
| WO | WO0230426 A1 | 4/2002 |
| WO | WO03035077 A1 | 5/2003 |
| WO | WO2004046115 A1 | 6/2004 |
| WO | WO2005087759 A | 9/2005 |
| WO | WO2005113509 A1 | 12/2005 |
| WO | WO2006027694 A1 | 3/2006 |
| WO | WO2006030807 A1 | 3/2006 |
| WO | WO2006033422 A1 | 3/2006 |
| WO | WO2006060712 A2 | 6/2006 |
| WO | WO2006083553 A | 8/2006 |

OTHER PUBLICATIONS

Asante-Appiah E et al. HIV-1 Integrase: Structural Organization, Conformational Changes, and Catalysis. Advances in Virus Research 52:351-369 (1999).
Chi G et al. Inhibition of the strand transfer step of HIV-1 integrase by non-natural dinucleotides. Bioorganic & Medicinal Chemistry Letters 14:4815-4817 (2004).
Chi G et al. A novel diketo phosphonic acid that exhibits specific, strand-transfer inhibition of HIV integrase and anti-HIV activity. Bioorganic & Medicinal Chemistry Letters 17:1266-1269 (2007).
DeClercq E. Toward Improved Anti-HIV Chemotherapy: Therapeutic Strategies for Intervention with HIV Infections. Journal of Medicinal Chemistry 38:2491-2517 (1995).
DeClercq E. In Search of a Selective Antiviral Chemotherapy. Clinical Microbiology Reviews 10:674-693 (1997).
De Clercq E. Strategies in the Design of Antiviral Drugs. Nature Reviews: Drug Discovery 1:13-25 (2002).
De Clercq E. HIV-chemotherapy and -prophylaxis: new drugs, leads and approaches. The International Journal of Biochemistry & Cell Biology 36:1800-1822 (2004).
De Clercq E. New Approaches toward Anti-HIV Chemotherapy. Journal of Medicinal Chemistry 48:1297-1313 (2005).
Esposito D et al. HIV Integrase Structure and Function. Advances in Virus Research V52:319-333 (1999).
Fauci As. The Human Immunodeficiency Virus: Infectivity and Mechanisms of Pathogenesis. Science 239:617-622 (1988).
Frankel Ad et al. HIV-1: Fifteen Proteins and an RNA. Annual Review of Biochemistry 67:1-25 (1998).
Grobler Ja et al. Diketo acid inhibitor mechanism and HIV-1 integrase: Implications for metal binding in the active site of phosphotransferase enzymes. Proceedings of the National Academy of Sciences USA 99:6661-6666 (2002).
Johnson Sc et al. Advances in HIV / AIDS Therapy. Advances in Internal Medicine 45:1-40 (2000).
Katz Ra et al. The Retroviral Enzymes. Annual Review of Biochemistry 63:133-173 (1994)).
Kelly Tr et al. Bisubstrate reaction templates. Examination of the consequences of identical versus different binding sites. Journal of the American Chemical Society 112:8024-8034 (1990).
Kowalski P. Electrophilic Benzylation of 2-Aminopyridine Ring. Journal of Heterocyclic Chemistry 28:875-879 (1991).

(Continued)

*Primary Examiner*—Zinna N Davis
(74) *Attorney, Agent, or Firm*—Henry D. Coleman; R. Neil Sudol; William J. Sapone

(57) ABSTRACT

A new class of diketo acids constructed on pyridinone scaffolds, designed as inhibitors of HIV replication through inhibition of HIV integrase, is described. These compounds are useful in the prevention or treatment of infection by HIV and in the treatment of AIDS and ARC, either as the compounds, or as pharmaceutically acceptable salts, with pharmaceutically acceptable carriers, used alone or in combination with antivirals, immunomodulators, antibiotics, vaccines, and other therapeutic agents, especially other anti-HIV compounds (including other integrase-based anti-HIV agents). Methods of treating AIDS and ARC and methods of treating or preventing infection by HIV are also described.

48 Claims, No Drawings

OTHER PUBLICATIONS

Marchand C et al. Structural Determinants for HIV-1 Integrase Inhibition by beta-Diketo Acids. The Journal of Biological Chemistry 277:12596-12603 (2002).
Miller Md et al. New antiretroviral agents: looking beyond protease and reverse transcriptase. Current Opinion in Microbiology 4:535-539 (2001).
Nair V. HIV integrase as a target for antiviral chemotherapy. Reviews in Medical Virology 12:179-193 (2002).
Nair V. Antiviral Isonucleosides: Discovery, Chemistry and Chemical Biology. in "Recent Advances in Nucleosides: Chemistry and Chemotherapy" C.K. Chu, ed., Elsevier Science B.V., Netherlands, 2002; pp. 149-166.
Nair V. Novel Inhibitors of HIV Integrase: The Discovery of Ppotential Anti-HIV Therapeutic Agents. Current Pharmaceutical Design 9:2553-2565 (2003).
Nair V. Novel Inhibitors of HIV Integrase: The Discovery of Potential Anti-HIV Therapeutic Agents. Frontiers in Medicinal Chemistry 2:3-20 (2005).
Nair V et al. HIV Integrase Ingibitors with Nucleobase Scaffolds: Discovery of a Highly Potent Anti-HIV Agent. Journal of Medicinal Chemistry 49:445-447 (2006).
Nair V et al. Beta-Diketo acids with purine nucleobase scaffolds: Novel, selective inhibitors of the strand transfer step of HIV integrase. Bioorganic & Medicinal Chemistry Letters 16:1920-1923 (2006).
Nair V et al. Conceptually Novel HIV Integrase Inhibitors with Nucleobase Scaffolds: Discoveery of a Highly Potent Anti-HIV Agent. Antiviral Research 70:A26 (2006).
Pais Gcg et al. Structure Activity of 3-Aryl-1,3-diketo-Containing Compounds as HIV-1 Integrase Inhibitors. Journal of Medicinal Chemistry 45:3184-3194 (2002).
Pommier Y et al. Integrase Inhibitors to Treat HIV / AIDS. Nature Reviews: Drug Discovery 4:236-248 (2005).
Sato M et al. Novel HIV-1 Integrase Inhibitors Derived from Quinolone Antibiotics. Journal of Medicinal Chemistry 49:1506-1508 (2006).
Sechi M et al. Design and Synthesis of Novel Indole beta-Diketo Acid Derivatives as HIV-1 Integrase Inhibitors. Journal of Medicinal Chemistry 47:5298-5310 (2004).
Spivey Ac et al. Axially Chiral Analogues of 4-(Dimethylamino)pyridine: Novel Catalysts for Nonenzymatic Enantioselective Acylations. Journal of Organic Chemistry 65:3154-3159 (2000).
Taktakishvili M et al. Recognition and Inhibition of HIV Integrase by Novel Dinucleotides. Journal of the American Chemical Society 122:5671-5677 (2000).
Wai Js et al. 4-Aryl-2,4-dioxobutanoic Acid Inhibitors of HIV-1 Integrase and Viral Replication in Cells. Journal of Medicinal Chemistry 43:4923-4926 (2000).
Zhang X et al. Azido-Containing Aryl beta-Diketo Acid HIV-1 Integrase Inhibitors. Bioorganic & Medicinal Chemistry Letters 13:1215-1219 (2003).

PYRIDINONE DIKETO ACIDS: INHIBITORS OF HIV REPLICATION

RELATED APPLICATIONS AND GRANT SUPPORT

This application claims the benefit of priority of provisional application No. U.S. 60/831,990, filed Jul. 19, 2006, and provisional application Nos. U.S. 60/920,196 and U.S. 60/920,197, filed Mar. 27, 2007, both entitled, "Pyridinone Diketo Acids: Inhibitors of HIV Replication", each of which applications is incorporated by reference in its entirety herein.

The work leading to the instant patent application was supported in part by a grant from the National Institutes of Health, award number A143181. Consequently, the United States government retains certain rights in the invention.

FIELD OF THE INVENTION

The present invention relates to the field of antiviral therapy, in particular the treatment of HIV infections in humans, including combination therapy.

BACKGROUND OF THE INVENTION

The human immunodeficiency virus, HIV, encodes three key viral enzymes through its pol gene and these enzymes are critical for the replication of this virus [Fauci, Science, 239, 617-622 (1988); Katz & Skalka, Annu. Rev. Biochem., 63, 133-173 (1994); Frankel, Annu. Rev. Biochem., 67, 1-25 (1998)]. For this reason, these enzymes of the pol gene have been targeted as potential sites of attack in the development of HIV antiviral chemotherapeutic agents [De Clercq, J. Med. Chem. 38, 2491-2517 (1995); Clin. Microbiol. Rev., 10, 674-693 (1997); De Clercq, Nature Reviews: Drug Discovery, 11, 13-25 (2002); De Clercq, J. Med. Chem. 48, 1297-1313 (2005)]. Drug discovery involving two of these enzymes, HIV reverse transcriptase (RT) and HIV protease (PR), and subsequent clinical applications of some of these therapeutic agents in combination therapy for the treatment of acquired immunodeficiency syndrome (AIDS) and AIDS related complex (ARC) in HAART (highly-active antiretroviral therapy) have suggested that this methodology of targeting key viral enzymes represents a useful approach in antiviral chemotherapy [Johnson & Gerber, in "Advances in Internal Medicine," vol. 44. Mosby: St. Louis, 1-40 (2000); De Clercq, Nature Reviews: Drug Discovery, 11, 13-25 (2002); Miller & Hazuda, Current Opinion in Microbiology, 4, 535-539 (2001); Asante-Appiah & Skalka, Adv. Virus Res., 52, 351-369 (1999); Nair, in "Recent Advances in Nucleosides: Chemistry and Chemotherapy," Elsevier Science: Netherlands, 149-166 (2002); DeClercq, Intl. J. Biochem. Cell Biol. 36, 1800-1822 (2004)]. While HIV RT and HIV PR have been extensively studied with respect to therapeutics, the third enzyme of the pol gene, HIV integrase, has received much less consideration [Miller & Hazuda, Current Opinion in Microbiology, 4, 535-539 (2001); Nair, Rev. Med. Virol., 12, 179-193 (2002); Nair, Current Pharmaceutical Design, 9, 2553-2565 (2003); Pommier, et al., Nature Rev. Drug Discovery 4, 236-248 (2005); Nair, Frontiers in Med. Chem. 2, 3-20 (2005)].

At present there are no drugs in clinical use for HIV/AIDS where the mechanism of action is inhibition of HIV integrase. HIV-1 integrase is a protein of 32 kDa encoded at the 3'-end of the pol gene [Asante-Appiah & Skalka, Adv. Virus Res., 52, 351-369 (1999); Esposito & Craigie, Adv. Virus Res., 52, 319-333 (1999)]. It is involved in the integration of HIV DNA into the host cell chromosome. Because integrase has no human counterpart and because it plays the significant role of completing the invasion of the human cell cell by HIV, it is an attractive target for the discovery of inhibitors of therapeutic potential.

Incorporation of HIV DNA into host chromosomal DNA in the cell nucleus catalyzed by integrase apparently occurs by a specifically defined sequence of 3'-processing or tailoring and strand transfer/integration reactions [Asante-Aplpiah & Skalka, Adv. Virus Res., 52, 351-369 (1999); Esposito & Craigie Adv. Virus Res., 52, 319-333 (1999)]. Prior to the initiation of the integration process, there is assembly of viral DNA, previously produced by reverse transcription, on the integrase. HIV integrase recognizes specific sequences in the LTRs of viral DNA. Following assembly of viral DNA on integrase, the processing of viral DNA occurs where there is site specific endonuclease activity and two nucleotides are cleaved off from each 3'-end of the double helical viral DNA to produce the tailored viral DNA recessed by two nucleotides and bearing a terminal CAOH-3'. For this initial 3'-processing step, integrase apparently activates the phosphodiester bond towards cleavage. The recessed viral DNA thus produced is joined in the next step to host cell DNA in the nucleus through a trans-esterification reaction. In this step, integrase positions the 3'-OH end of the viral DNA for nucleophilic attack on the phosphodiester bond in the host DNA. In the subsequent step, there is cleavage of 4-6 bp in host DNA and the coupling involves the joining of processed CAOH-3' viral DNA ends to the 5'-phosphate ends of the host DNA. Finally, there is repair of the resulting gapped intermediate mediated by host cell enzymes, although a role here for the integrase is also possible.

A variety of compounds are inhibitors of HIV integrase but some of these compounds are non-specific inhibitors of the enzyme while evidence suggests that others may possess some specificity. The various classes include nucleotides, oligonucleotides, dinucleotides, and miscellaneous small molecules including heterocyclic systems, natural products, diketo acids, sulfones and others [Nair, Rev. Med. Virol., 12, 179-193 (2002); Nair, Current Pharmaceutical Design, 9, 2553-2565 (2003); Chi and Nair, Bioorg. Med. Chem. Lett. 14, 4815-4817 (2004); Nair and coworkers, J. Am. Chem. Soc., 122, 5671-5677 (2000)].

The class of previously studied compounds that are most directly relevant to this patent are diketo acids with aryl or heteroaryl substitutions. Some of these compounds are inhibitors of HIV integrase, but most commonly of only the strand transfer step. The integrase inhibition data have been reported in several scientific publications [Wai, et al., "4-Aryl-2,4-dioxobutanoic acid inhibitors of HIV-1 integrase and viral replication in cells," J. Med. Chem. 43, 4923-4926 (2000); Pais, G. C. G., et al., "Structure activity of 3-aryl-1, 3-diketo-containing compounds as HIV-1 integrase inhibitors," J. Med. Chem. 45, 3184-3194 (2002); Marchand, C., et al., "Structural determinants for HIV-1 integrase inhibition by β-diketo acids," J. Biol. Chem. 277, 12596-12603 (2002); Sechi, M., et al., "Design and synthesis of novel indole beta-diketo acid derivatives as HIV-1 integrase inhibitors," J. Med. Chem. 47, 5298-5310 (2004); Zhang, et al., "Azido-containing aryl β-keto acid HIV-1 integrase inhibitors," Bioorg. Med. Chem. Lett. 13, 1215-1219 (2003), Nair, et al., "HIV integrase inhibitors with nucleobase scaffolds: discovery of a highly potent anti-HIV agent," J. Med. Chem. 49, 445-447 (2006); Nair, et al., "Conceptually novel HIV integrase inhibitors with nucleobase scaffolds: discovery of a highly potent anti-HIV agent," Antiviral Res. 70, A26 (2006); Sato, et al., "Novel HIV-1 integrase inhibitors derived from quinolone antibiotics," *J. Med. Chem.* 49, 1506-1508 (2006); Nair et al., "Beta-diketo acids with purine nucleobase scaffolds: novel selective inhibitors of the strand transfer step of HIV integrase," *Bioorg. Med. Chem. Lett.* 16, 1920-1923 (2006), Chi et al., "A novel diketo phosphonic acid that exhibits specific, strand-transfer inhibition of HIV integrase and anti-HIV activity," *Bioorg. Med. Chem. Lett.* 17, 1266-1269 (2007)]. Other publications in the area are of peripheral relationship to this patent application.

The mechanism of inhibition of HIV integrase by diketo acids may be the result of interaction of the functional groups on these compounds with metal ions in the active site of integrase, resulting in a functional sequestration of these critical metal cofactors [Grobler, J. A., et al., *Proc. Natl. Acad. Sci. U.S.A.* 99, 6661-6666 (2002)].

Related patents to this application are: Selnick, H. G. et al., (Merck & Co. Inc.), "Preparation of nitrogen-containing 4-heteroaryl-2,4-dioxobutyric acids useful as HIV integrase inhibitors," WO 9962513; Young, S. D., et al., (Merck & Co. Inc.), "Preparation of aromatic and heteroaromatic 4-aryl-2, 4-dioxobutyric acid derivatives useful as HIV integrase inhibitors," WO 9962897; Fujishita, T., et al., Yoshinaga, T., et al. (Shionogi & Co. Ltd.), "Preparation of aromatic heterocycle compounds having HIV integrase inhibiting activities," WO 0039086; Akihiko, S., (Shionogi & Co. Ltd.), "Medicinal compositions containing propenone derivatives," WO 0196329; Payne, L. S., et al., (Merck & Co. Inc.; Tularik, Inc.), "Preparation of 1,3-diaryl-1,3-propanediones as HIV integrase inhibitors," WO 0100578; Egbertson, M., et al., (Merck & Co. Ltd.), "HIV integrase inhibitors," WO 9962520. Some of the patents cited above are closely related. However, none of the patents or publications describe the class of compounds according to the present invention. Other patents of peripheral relationship to this invention are: Anthony, et al., (Merck & Co. Inc.), "Aza and polyaza-napthalenyl-carboxamides useful as HIV integrase inhibitors," WO 02/30426; Sato, et al., (Japan Tobacco Inc.), "Preparation of 4-oxoquinoline derivatives as HIV integrase inhibitors," WO 2004046115; Sato, et al., (Japan Tobacco Inc.), "Novel 4-oxoquinoline compounds and use thereof as HIV integrase inhibitors," WO 2005113509; Crescenzi, et al., (Instituto Di Richerche Di Biologia Molecolare P. Angeletti SPA) "Preparation of N-substituted hydroxypyrimidinone carboxamide inhibitors of HIV integrase," WO 2003035077; Belyk, et al., (Merck & Co. Inc., Instituto Di Richerche Di Biologia Molecolare P. Angeletti SPA), "Preparation of N-(4-fluorobenzyl)-5-hydroxy-1-methyl-2-(1-methyl-1-{[(5-methyl-1,3,4-oxadiazol-2-yl)carbonyl]amino}ethyl)-6-oxo-1, 6-dihydropyrimidine-4-carboxamide potassium salts as HIV integrase inhibitors," WO 2006060712; Sato, et al., (Japan Tobacco Inc.), "Preparation of quinolizinone compounds as HIV integrase inhibitors," WO 2006033422; Yoshida, et al., (Shionogi & Co. Ltd.), "Preparation of carbamoyl-pyridinone derivative having HIV integrase inhibitory activity," WO 2006030807; Dress, et al., (Pfizer, Inc.), "Preparation of N-hydroxy pyrrolopyridinecarboxamides as inhibitors of HIV integrase," WO 2006027694; Naidu, et al., (Bristol-Myers Squibb Co.), "HIV integrase inhibitors," US 2005/0261322; Naidu, et al., (Bristol-Myers Squibb Co.), "Bicyclic heterocycles as HIV integrase inhibitors," US 2005/0267105; Naidu, et al., (Bristol-Myers Squibb Co.), "Bicyclic heterocycles as HIV integrase inhibitors," US 2006/0199956. While some of the patents cited above are more related than others, none of the patents or publications describe the class of compounds according to the present invention.

The class of compounds described by us in this invention are inhibitors of HIV-1 integrase and also possess in vitro anti-HIV activity. An example of the anti-HIV data in PBMC for the clinical isolate, $HIV_{NL4-3}$, in PBMC for one of our compounds, 4-(1,5-dibenzyl-1,2-dihydro-2-oxopyridin-3-yl)-2-hydroxy-4-oxobut-2-enoic acid, (8) and AZT in the same study is given below.

Compound 8 $EC_{95}$ 0.61 µM, $CC_{95}$>200 µM, Therapeutic Index (TI)>330

AZT $EC_{95}$ 9.42 nM, $CC_{95}$>1 µM, Therapeutic Index (TI)> 106

At pH 7.4, the half life ($t_{1/2}$) of compound 8 is >41 hours. The $t_{1/2}$ in pooled human liver microsome for compound 8 is >6 hours.

SUMMARY OF THE INVENTION

A new class of diketo acids constructed on pyridinone scaffolds, and designed as inhibitors of HIV replication through inhibition of HIV integrase, is described. These compounds can be represented by the general formula I (and includes tautomers, regioisomers and geometric isomers, as well as pharmaceutically acceptable salts thereof, where applicable), in which the moiety illustrated as a square is a molecular scaffold made up of a pyridinone derivative. These compounds have application in the prevention or treatment of infection by HIV and the treatment of AIDS and ARC, either as the compounds, or as their pharmaceutically acceptable salts, with pharmaceutically acceptable carriers, used alone or in combination with antivirals, immunomodulators, antibiotics, vaccines, and other therapeutic agents, especially other anti-HIV compounds (including other anti-HIV integrase agents), which can be used to create combination anti-HIV cocktails. Methods of treating AIDS and ARC and methods of treating or preventing infection by HIV are also described.

The present invention further relates in preferred aspects to the use of at least one of the above compounds in combination with at least one additional anti-HIV agent as otherwise described herein.

DETAILED DESCRIPTION OF THE INVENTION

The following terms shall be used throughout the specification to describe the present invention. Unless otherwise indicated, a term used to describe the present invention shall be given its ordinary meaning as understood by those skilled in the art.

The term "compound", as used herein, unless otherwise indicated, refers to any specific chemical compound disclosed herein and includes tautomers, regioisomers, geometric isomers, and where applicable, optical isomers thereof, as well as pharmaceutically acceptable salts and hydrates thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The breadth of the term "compound" shall be construed within the context of the use of the term.

The term "patient" or "subject" is used throughout the specification to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective" is used herein, unless otherwise indicated, to describe an amount of a compound or composition or component which, in context, is used to produce or effect an intended result, whether that result relates to the treatment of a viral, microbial or other disease state, disorder or condition associated with HIV, ARC or AIDS or alternatively, is used to produce another compound, agent or composition. This term subsumes all other effective amount or effective concentration terms which are otherwise described in the present application.

The term "scaffold" is used throughout the specification to mean a pyridinone chemical structure containing at least four substituents at five substitutable positions on this scaffold, one of which is a ketoacid as otherwise defined herein and the other four of which $R^1$, $R^2$, $R^3$ and $R^4$ are as defined herein.

The term "heteroaryl" shall mean a 5 or 6-membered heteroaromatic ring containing 1 to 2 heteroatoms selected from oxygen, nitrogen and sulfur, which heteroaromatic ring is optionally substituted with from 1 to 3 substituents such as halogen, hydroxyl, $C_{1-3}$ alkyl, $C_{1-3}$ alkoxy and $CF_3$. The terms heteroaryl and "heteroaromatic ring" are used interchangeably herein.

The term "human immunodeficiency virus" or "HIV" shall be used to describe human immunodeficiency viruses 1 and 2 (HIV-1 and HIV-2).

The terms "ARC" and "AIDS" refer to syndromes of the immune system caused by the human immunodeficiency virus, which are characterized by susceptibility to certain diseases and T cell counts which are depressed compared to normal counts. HIV progresses from Category 1 (Asymptomatic HIV Disease) to Category 2 (ARC), to Category 3 (AIDS), with the severity of the disease.

A Category 1 HIV infection is characterized by the patient or subject being HIV positive, asymptomatic (no symptoms) and having never had fewer than 500 CD4 cells. If the patient has had any of the AIDS-defining diseases listed for categories 2 (ARC) or 3 (AIDS), then the patient is not in this category. If the patient's t-cell count has ever dropped below 500, that patient is considered either Category 2 (ARC) or Category 3 (AIDS).

A Category 2 (ARC) infection is characterized by the following criteria: The patient's T-cells have dropped below 500 but never below 200, and that patient has never had any Category 3 diseases (as set forth below) but have had at least one of the following defining illnesses—

Bacillary angiomatosis
Candidiasis, oropharylgeal (thrush)
Candidiasis, vulvovaginal; persistent, frequent, or poorly responsive to therapy
Cervical dysplasia (moderate or severe)/cervical carcinoma in situ
Constitutional symptoms, such as fever (38.5 C) or diarrhea lasting longer than 1 month
Hairy leukoplakia, oral
Herpes zoster (shingles), involving at least two distinct episodes or more than one dermatome
Idiopathic thrombocytopenic purpura
Listeriosis
Pelvic inflammatory disease, particularly if complicated by tubo-ovarian abscess
Peripheral neuropathy According to the U.S. government, in Category 2 ARC, the immune system shows some signs of damage but it isn't life-threatening.

A Category 3 (AIDS) infection is characterized by the following criteria:
your T-cells have dropped below 200 or
you have had at least one of the following defining illnesses—
Candidiasis of bronchi, trachea, or lungs
Candidiasis, esophageal
Cervical cancer, invasive**
Coccidioidomycosis, disseminated or extrapulmonary
Cryptococcosis, extrapulmonary
Cryptosporidiosis, chronic intestinal (greater than 1 month's duration)
Cytomegalovirus disease (other than liver, spleen, or nodes)
Cytomegalovirus retinitis (with loss of vision)
Encephalopathy, HIV-related
Herpes simplex: chronic ulcer(s) (greater than 1 month's duration); or bronchitis, pneumonitis, or esophagitis
Histoplasmosis, disseminated or extrapulmonary
Isosporiasis, chronic intestinal (greater than 1 month's duration)
Kaposi's sarcoma
Lymphoma, Burkitt's (or equivalent term)
Lymphoma, immunoblastic (or equivalent term)
Lymphoma, primary, of brain
*Mycobacterium avium* complex or *M. kansasii*, disseminated or extrapulmonary
*Mycobacterium tuberculosis*, any site (pulmonary** or extrapulmonary)
*Mycobacterium*, other species or unidentified species, disseminated or extrapulmonary
*Pneumocystis carinii* pneumonia
Pneumonia, recurrent**
Progressive multifocal leukoencephalopathy
*Salmonella septicemia*, recurrent
Toxoplasmosis of brain
Wasting syndrome due to HIV The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time (but not necessarily at all times).

The term "independently" is used herein to indicate that the variable, which is independently applied, varies independently from application to application.

The present invention is directed to compounds of the general molecular formula I, combinations thereof, or pharmaceutically acceptable salts thereof, in the inhibition of HIV integrase, the prevention or treatment of HIV infections and in the treatment of AIDS and ARC. Compounds of formula I are defined as follows:

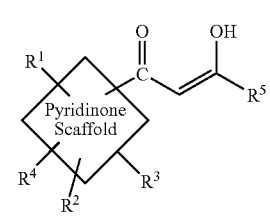

I including tautomers, regioisomers, geometric isomers, and where applicable, optical isomers thereof, and pharmaceutically acceptable salts thereof, wherein the pyridinone scaffold and R groups are defined as:

diketo acids with the two pyridinone scaffolds shown;

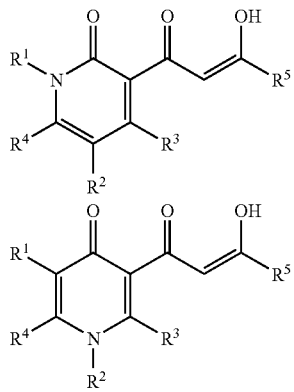

$R^1$ and $R^2$ are independently:
a) H,
b) $C_{1-6}$ alkyl,
c) $C_{1-6}$ fluoroalkyl,
d) $C_{1-6}$ alkyl $S(O)_nR$, wherein n selected from 0-2, R is selected from $C_{1-3}$ alkyl, phenyl and substituted phenyl with substituents selected from:
   1) halogen,
   2) hydroxy,
   3) $C_{1-3}$ alkyl,
   4) $C_{1-3}$ alkoxy,
   5) $CF_3$,
e) $C_{5-6}$ cycloalkyl with 1 to 3 substituents selected from:
   1) halogen,
   2) hydroxy,
   3) $C_{1-3}$ alkyl,
   4) $C_{1-3}$ alkoxy,
   5) $CF_3$,
f) $C_{1-6}$ alkenyl,
g) $C_{1-6}$ alkyl $CO_nR^a$, wherein n selected from 1 and 2, $R^a$ selected from:
   1) $C_{1-6}$ alkyl,
   2) H,
h) Phenyl,
i) Substituted phenyl with 1 to 3 substituents selected from:
   1) halogen,
   2) hydroxy,
   3) $C_{1-3}$ alkyl,
   4) $C_{1-3}$ alkoxy,
   5) $CF_3$,
j) Benzyl,
k) Substituted benzyl with 1 to 3 substituents selected from:
   1) halogen,
   2) hydroxy,
   3) $C_{1-3}$ alkyl,
   4) $C_{1-3}$ alkoxy,
   5) $CF_3$,
l) $C_{2-6}$ alkyl substituted with phenyl,
m) $C_{2-6}$ alkyl substituted with phenyl, the phenyl group may be substituted with 1 to 3 substituents selected from:
   1) halogen,
   2) hydroxy,
   3) $C_{1-3}$ alkyl,
   4) $C_{1-3}$ alkoxy,
   5) $CF_3$,
n) $R^b$
o) $C_{1-6}$ alkyl substituted with $R^b$, Wherein each $R^b$ is 5 or 6 membered heteroaromatic ring containing 1 to 2 heteroatoms selected from oxygen, nitrogen and sulfur, the ring could be substituted or not on carbon or nitrogen with 1 to 3 substituents selected from:
1) halogen,
2) hydroxy,
3) $C_{1-3}$ alkyl,
4) $C_{1-3}$ alkoxy,
5) $CF_3$,
$R^3$ and $R^4$ are independently selected from:
a) H,
b) $C_{1-6}$ alkyl,
c) Halogen,
d) Hydroxyl,
e) Phenylthio,
f) Substituted phenylthio with 1 to 3 substituents selected from:
   1) halogen,
   2) hydroxy,
   3) $C_{1-3}$ alkyl,
   4) $C_{1-3}$ alkoxy,
   5) $CF_3$,
g) Benzyl,
h) Substituted benzyl with 1-3 substituents selected from:
   1) halogen,
   2) hydroxy,
   3) $C_{1-3}$ alkyl,
   4) $C_{1-3}$ alkoxy,
   5) $CF_3$,
$R^5$ is selected from:
a) $CO_2R^c$, wherein $R^c$ is selected from:
   1) $C_{1-6}$ alkyl,
   2) H,
   3) sodium or other pharmaceutical acceptable salt,
b) $P(O)(OR^d)(OR^e)$, wherein $R^d$ and $R^e$ could be same or not and that are selected from:
   1) $C_{1-6}$ alkyl,
   2) H,
   3) sodium or other pharmaceutical acceptable salt.

Certain preferred embodiments include compounds which are based on the 2-pyridinone (pyridin-2-one) scaffold in which the diketo acid moiety is at the 3-position of the pyridinone ring:

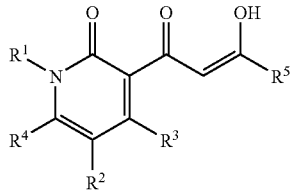

wherein $R^1$ and $R^2$ are independently benzyl groups or independently substituted benzyl groups with 1 to 3 substituents on the phenyl rings selected from fluorine, chlorine, $C_{1-4}$ alkyl, $C_{2-4}$ alkenyl, methoxy;

wherein $R^3$ is H, $C_{1-3}$ alkyl, $C_{2-3}$ alkenyl, fluorine, chlorine, methoxy;

wherein $R^4$ is H, F, Cl, OH wherein $R^5$ is $CO_2H$ or $P(O)(OH)_2$ or a pharmaceutically acceptable salt thereof.

Also included within the present invention are pharmaceutical compositions, preferably useful for inhibiting HIV integrase, comprising of an effective amount of a compound of this invention, and a pharmaceutically acceptable carrier, additive or excipient. Pharmaceutical compositions useful for treating infection by HIV or for treating AIDS or ARC are also included by the present invention. The present invention also includes methods for inhibiting the viral enzyme, HIV integrase, and a method of inhibiting HIV growth or replication, or treating an HIV infection or for treating AIDS or ARC. In addition, the present invention is directed to a pharmaceutical composition comprising, in combination, a therapeutically effective amount of a compound of the present invention in combination with a therapeutically effective amount of an agent for the treatment of AIDS selected from (i) an AIDS or HIV antiviral agent, (ii) an anti-infective agent, (iii) an immunomodulator, (iv) other useful therapeutic agents including antibiotics and other antiviral agents.

The compounds of the present invention may have regioisomers with respect to pyridinone scaffold and $R^1$, $R^2$, $R^3$ and $R^4$ and these regioisomeric forms are included in the present invention. The compounds may have asymmetric centers and may occur as optical isomers and all of these isomeric forms are included in the present patent invention. The compounds may have geometric isomers and these forms are included in the present invention.

PLEASE PROVIDE PREFERRED EMBODIMENTS (substitutents), If APPLICABLE, for R1, R2, R3, R4, R5, Ra, Rb, Rc, Rd, Re, etc.

Tautomeric forms may also exist with compounds of the present invention. Thus, the terminology "and tautomers thereof" is used in describing tautomeric forms of compounds of formula I such as Ia and Ib (shown below). By naming compounds as being represented by the general formula I and tautomers thereof, it is understood that for the purposes of the present invention that tautomers Ia and Ib are also included. Similarly, by referring to compound (Ia), it is understood for the purposes of the present application that tautomers (I) and (Ib) are also intended. The same holds true for references to tautomer (Ib).

occurrence is independent of its definition at every other occurrence. Combinations of pyridinones and variables are permissible only if, in context, such combinations result in stable compounds.

The compounds of the present invention are useful inter alia, in the inhibition of HIV integrase, the prevention or treatment of infection by HIV and in the treatment of the disease known as AIDS. Treating AIDS or preventing or treating infection by HIV is defined as including the treatment of a wide range of states of HIV infection: AIDS, ARC and actual or potential exposure to HIV (e.g., through blood transfusion, exchange of body fluids, bites, needle punctures, exposure to infected patient blood during medical or dental procedures, and other means).

Other applications are also part of this invention. For example, the compounds of this invention are useful in the preparation and execution of screening assays for antiviral compounds including in the isolation of viral enzyme mutants and in further understanding of the enzyme, HIV integrase.

The present invention also provides for the use of a compound of structural formula (I) to make a pharmaceutical composition useful for inhibiting HIV integrase and in the treatment of AIDS or ARC.

The compounds of the present invention may be administered in the form of "well-known pharmaceutically acceptable" salts. The latter is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, camsylate, mucate, carbonate, napsylate, chloride, nitrate, clavulanate, N-methylglucamine, citrate, ammonium salt, dihydrochloride, oleate, edetate, oxalate, edisylate, pamoate, estolate, palmitate, esylate, fumarate, phosphate, diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and others which can be used as a dosage form for modifying the solubility or

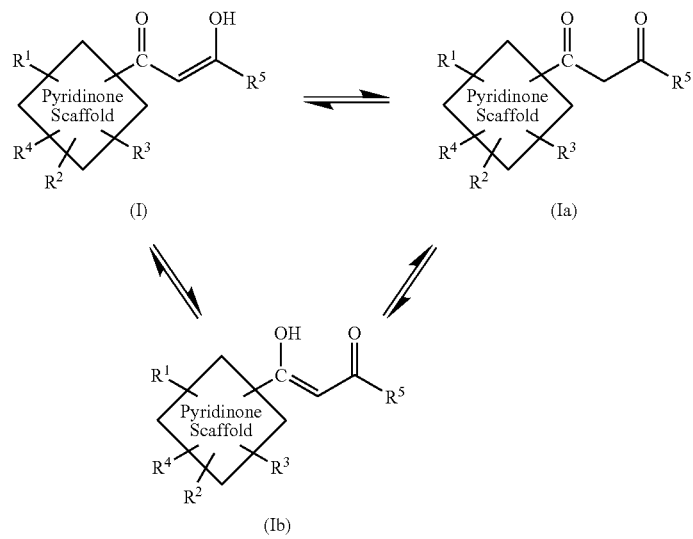

When the variables involving $R^1$, $R^2$, $R^3$, $R^4$ and $R^5$ occur more than once in any formula I, the definition on each hydrolysis characteristics or can be used in sustained release or pro-drug formulations. The pharmaceutically acceptable salts of this invention include those with counterions such as sodium, potassium, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

Also, in the case of a carboxylic acid (—COOH) or an alcohol group being present, pharmaceutically acceptable esters can be employed, e.g., acetate, maleate, pivaloyloxymethyl and others, more preferably $C_1$-$C_{20}$ esters and those esters known in the art for improving solubility or hydrolysis characteristics for use as sustained release or pro-drug formulations. Pharmaceutically acceptable esters can also be employed in the case where a phosphonic acid group [—PO(OH)$_2$] is present. Diketo phosphonic acids attached to pyridinone scaffolds are also part of this invention.

Therapeutically effective amounts of the compounds of the present invention may be administered to patients orally, parenterally, by inhalation spray, or rectally, in dosage unit formulations containing pharmaceutically-acceptable carriers, adjuvants and vehicles including nanoparticle drug delivery approaches. The term "pharmaceutically acceptable" is meant to infer that the carrier, diluent, excipient or other additive must be compatible with the other ingredients of the formulation and not deleterious to the patient or recipient.

Pharmaceutical compositions may be in the form of orally-administrable suspensions or tablets, nasal sprays and injectable preparations (injectable aqueous or oleagenous suspensions or suppositories). This method of treatment is part of the invention. The administration approaches used (orally as Solution or suspension, immediate release tablets, nasal aerosol or inhalation, injectable solutions or suspensions or rectally administered in the form of suppositories) involve techniques that are well-known in the art of pharmaceutical formulation.

The compounds of this invention can be administered orally to humans in a preferred form (such as tablets) and in a preferred dosage range of about 0.1 to 200 mg/kg body weight in divided doses. The specific dose level and frequency of dosage for any particular patient may be varied and will depend upon a variety of factors including compound activity, compound metabolism and duration of action, patient age, body weight, general health, sex, diet, mode and time of administration, rate of excretion, drug combination, the severity of the particular condition, and the condition of the patient undergoing therapy.

The present invention also includes therapeutically effective combinations of the HIV integrase inhibitor compounds of formula I with one or more other therapeutic agents such as AIDS antivirals, other antiviral agents, immunomodulators, antiinfectives, antibiotics, vaccines or other therapeutic agents. Some examples are given below.

| ANTIVIRAL AGENTS, ANTI-INFECTIVES, IMMUNOMODULATORS, OPPORTUNISTIC INFECTION DRUGS, OTHER RELEVANT DRUGS IN AIDS | | |
|---|---|---|
| Drug Name | Manufacturer | Therapeutic Use |
| 097 | Hoechst/Bayer | HIV infection, AIDS, ARC (NNRT inhibitor) |
| Amprenivir 141W94, GW141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences, | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR 177 | Aronex Pharm | HIV infection, AIDS, ARC |
| Beta-fluoro-ddA | National Cancer Institute | AIDS-associated diseases |
| BMS-232623 (CGP-73547) | Bristol-Myers Squibb/Novartis | HIV infection, AIDS, ARC (protease inhibitor) |
| BMS-234475 (CGP-61755) | Bristol-Myers Squibb/Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |

-continued

ANTIVIRAL AGENTS, ANTI-INFECTIVES, IMMUNOMODULATORS, OPPORTUNISTIC INFECTION DRUGS, OTHER RELEVANT DRUGS IN AIDS

| Drug Name | Manufacturer | Therapeutic Use |
| --- | --- | --- |
| Curdlan sulfate | AJI Pharma USA | HIV infection |
| Cytomegalovirus Immune globin | MedImmune | CMV retinitis |
| Cytovene Ganciclovir | Syntex | Sight threatening CMV CMV Retinitis |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP-266) | DuPont Merck | HIV infection, AIDS, ARC (non-nucleoside RT inhibitor |
| EL10 | Elan Corp, PLC (Gainesville, GA) | HIV infection |
| Famciclovir | Smith Kline | Herpes zoster, herpes simplex |
| FTC | Emory University | HIV infection, AIDS, ARC (RT inhibitor) |
| GS 840 | Gilead | HIV infection, AIDS, ARC (RT inhibitor) |
| HBY097 | Hoechst Marion Roussel | HIV infection, AIDS, ARC (non-nucleoside RT inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive; combination with AZT/ddI/ddC |
| ISIS-2922 | ISIS Pharmaceuticals | CMV retinitis |
| KNI-272 | Natl. Cancer Institute | HIV-associated diseases |
| Lamivudine, 3TC | Glaxo Wellcome | HIV infection, AIDS, ARC (RT inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CVV retinitis, HIV infection, other CMV |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | Asymptomatic HIV positive, LAS, ARC |
| VX-478 | Vertex | HIV infection, AIDS, ARC |
| Zalcitabine | Hoffmann-LaRoche | HIV infection, AIDS, ARC with AZT |
| Zidovudine; AZT | Glaxo Wellcome | HIV infection, AIDS, ARC, Kaposi's sarcoma, in combination with other therapies |

-continued

ANTIVIRAL AGENTS, ANTI-INFECTIVES, IMMUNOMODULATORS, OPPORTUNISTIC INFECTION DRUGS, OTHER RELEVANT DRUGS IN AIDS

| Drug Name | Manufacturer | Therapeutic Use |
|---|---|---|
| Tenofovir diisoproxil fumarate salt (Viread ®) | Gilead | HIV infection, AIDS, (RT inhibitor) |
| Combivir ® | GSK | HIV infection, AIDS, (RT inhibitor) |
| Abacavir succinate (or Ziagen ®) | GSK | HIV infection, AIDS, (reverse transcriptase inhibitor) |
| Fuzeon ® (or T-20) | Roche/Trimeris | HIV infection, AIDS, viral Fusion inhibitor |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki Immuno PHARM | Blocks HIV fusion with CD4+ cells |
| Gamma Interferon | Genentech | ARC, in combination w/TNF |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4-IgG | Genentech | AIDS, ARC |
| rCD4-IgG Hybrids | | AIDS, ARC |
| Recombinant Soluble Human CD4 | Biogen | AIDS, ARC |
| Interferon Alfa 2a | Hoffman-LaRoche | Kaposi's sarcoma, AIDS, AR, combination w/AZT |
| SK&F1-6528 Soluble T4 | Smith Kline | HIV infection |
| Thymopentin | Immunobiology Research Institute (Annandale, NJ) | HIV infection |
| Tumor Necrosis Factor (TNF) | Genentech | ARC, in combination w/gamma Interferon |
| AK602 | Kumamoto University Japan | HIV infection (entry and fusion inhibitor) |

-continued

ANTIVIRAL AGENTS, ANTI-INFECTIVES, IMMUNOMODULATORS, OPPORTUNISTIC INFECTION DRUGS, OTHER RELEVANT DRUGS IN AIDS

| Drug Name | Manufacturer | Therapeutic Use |
| --- | --- | --- |
| Alovudine | Medivir, UK Ltd. | HIV infection (nucleoside RT inhibitor) |
| Amdoxovir | RFS Pharma, LLC | Treatment of HIV and HBV infections (nucleoside RT Inhibitor) |
| AMD070 | AnorMED, Inc. | HIV infection (entry and fusion inhibitor) |
| Atazanavir (Reyataz) | Bristol - Myers Squibb | HIV infection (protease inhibitor) |
| AVX754 (apricitabine) | Avexa Ltd. | HIV infection (nucleoside RT inhibitor |
| Bevirimat | Panacos Pharmaceuticals | HIV infection (maturation inhibitor) |
| BI-201 | BioInvent | HIV infection (gene therapy, blocks HIV tat gene). |
| BMS-378806 | Bristol - Myers Squibb | HIV infection (entry inhibitor) |
| BMS-488043 | Bristol - Myers Squibb | HIV infection (entry and fusion inhibitor) |
| BMS-707035 | Bristol - Myers Squibb | HIV infection (integase inhibitor) |
| C31G | Cellegy Pharmaceuticals, Inc | HIV infection and other sexually transmitted diseases (STDs) |
| Carbopol 974P | ReProtect, LLC | Sexual transmission of HIV |
| Calanolide A | Sarawak MediChem Pharmaceuticals, Inc. | HIV infection (non-nucleoside RT inhibitor) |
| Carrageenan | FMC Biopolymer | HIV microbicide |
| Cellulose sulfate | Polydex Pharmaceuticals, Ltd. | Prevention of HIV infection and other sexually transmitted diseases |
| Cyanovirin-N | Cellegy Pharmaceuticals, Inc. | Prevention of sexual transmission of HIV infection |
| Darunavir | Tibotec | HIV infection (co-administered with ritonavir) |
| Delavirdine | Pfizer | HIV infection (non-nucleoside RT inhibitor) |
| Dextran sulfate | Ueno Fine Chemicals Industry, Ltd. | Prevention of transmission of HIV |
| Didanosine (Videx, Videx EC) | Bristol - Myers Squibb | HIV infection (nucleoside RT inhibitor) |
| Efavirenz | Bristol - Myers Squibb | HIV infection (non-nucleoside RT inhibitor) |
| Elvucitabine | Achillion Pharmaceuticals | HIV infection (nucleoside RT inhibitor) |
| Emtricitabine | Gilead Sciences | HIV infection (nucleoside RT inhibitor) |
| Fosamprenavir (Lexiva) | GlaxoSmithKline | HIV infection (protease inhibitor) |
| Fozivudine tidoxil | Heidelberg Pharma | HIV infection (entry and fusion inhibitor) |
| GS 9137 | Gilead Sciences | HIV infection (integase inhibitor) |
| GSK-873,140 (aplaviroc) | GlaxoSmithKline | HIV infection (entry and fusion inhibitor) |
| GSK-364735 | GlaxoSmithKline | HIV infection (integase inhibitor) |
| GW640385 (brecanavir) | GlaxoSmithKline | HIV infection (protease inhibitor) |
| HG0004 | Human Genome Sciences | HIV infection (entry and fusion inhibitor) |
| HGTV43 | Enzo Therapeutics | HIV infection (antisense drug) |
| Hydroxyethyl cellulose | Union Carbide | Prevent sexual transmission of HIV |
| INCB9471 | Incyte Corporation | HIV infection (entry and fusion inhibitor) |
| KP-1461 | Koronis Pharmaceuticals | HIV infection (nucleoside RT inhibitor) |
| Lopinavir | Abbott Laboratories | HIV infection (protease inhibitor) |

-continued

ANTIVIRAL AGENTS, ANTI-INFECTIVES, IMMUNOMODULATORS, OPPORTUNISTIC INFECTION DRUGS, OTHER RELEVANT DRUGS IN AIDS

| Drug Name | Manufacturer | Therapeutic Use |
| --- | --- | --- |
| Mifepristone (VGX410, RU486) | Viral Genomix | HIV infection (gene therapy, interferes with vpr) |
| MK-0518 | Merck | HIV infection (integase inhibitor) |
| PA-457 (bevirimat) | Panacos Pharmaceuticals, Inc. | Treatment of HIV (maturation inhibitor) |
| Poly(I)-Poly(C12U) (Ampligen) | Hemispherx Biopharma, Inc. | Biological response modifier |
| PPL-100 | Merck | HIV infection (protease inhibitor) |
| PRO 140 | Progenics Pharmaceuticals, Inc. | HIV infection (entry and fusion inhibitor) |
| PRO 542 | Progenics Pharmaceuticals, Inc. | HIV infection (entry and fusion inhibitor) |
| PRO 2000 | Indevus Pharmaceuticals, Inc. | Microbicide |
| Racivir | Pharmasset, Inc. | HIV infection (nucleoside RT inhibitor) |
| SCH-D (vicriviroc) | Schering - Plough Corp | HIV infection (entry and fusion inhibitor) |
| SP01A | Samaritan Pharmaceuticals | HIV infection (entry and fusion inhibitor) |
| SPL7013 | Starpharma | Microbicide |
| TAK-652 | Takeda | HIV infection (entry and fusion inhibitor) |
| Tipranavir (Aptivus) | Boehringer Ingelheim Pharmaceuticals | HIV infection (protease inhibitor) |
| TNX-355 | Tanox, Inc. | HIV infection (entry and fusion inhibitor) |
| TMC125 (etravirine) | Tibotec | HIV infection (non-nucleoside RT inhibitor) |
| UC-781 | Cellegy Pharmaceuticals, Inc | Microbicide |
| UK-427,857 (Maraviroc) | Pfizer | HIV infection (entry and fusion inhibitor) |
| Valproic acid | Abbott | Treating seizures in HIV infection |
| VRX496 | VIRxSYS | Gene therapy |
| Zalcitabine (Hivid) | Roche | HIV infection (nucleoside RT inhibitor) |
| Valganciclovir (Valcyte) | Roche | Antiviral (CMV retinitis in AIDS) |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine isethionate | Fisons Corporation | PCP prophylaxis |
| Spiramycin | Rhone-Poulenc | Cryptosporidial diarrhea |
| Intraconazole-R51211 | Janssen Pharm | Histoplasmosis; cryptococcal meningitis |
| Trimetrexate | Warner-Lambert | PCP |
| Daunorubicin | NeXstar, Sequus | Karposi's sarcoma |
| Recombinant Human Erythropoietin | Ortho Pharm. Corp. | Severe anemia assocated w/AZT therapy |
| Recombinant Human Growth Hormone | Serono | AIDS-related wasting, cachexia |
| Megestrol Acetate | Bristol-Myers Squibb | Treatment of anorexia associated w/AIDS |
| Testosterone | Alza, Smith Kline | AIDS-related wasting |
| Total Enteral Nutrition | Norwich Eaton Pharmaceuticals | Diarrhea and malabsorption in AIDS |

-continued

ANTIVIRAL AGENTS, ANTI-INFECTIVES, IMMUNOMODULATORS,
OPPORTUNISTIC INFECTION DRUGS, OTHER RELEVANT DRUGS IN AIDS

| Drug Name | Manufacturer | Therapeutic Use |
|---|---|---|
| Aldesleukin (Proleukin) | Chiron Corp | Biological response modifier |
| Amphotericin B (Abelecet, AmBisome, Amphocin, Amphotec, Fungizone) | Pfizer, Bristol - Myers Squibb | Antifungal |
| Azithromycin (Zithromax) | Pfizer | Antibacterial antibiotic |
| Calcium hydroxyapatite (Radiesse) | Bioform Medical, Inc. | Dermal filler |
| Doxorubicin (liposomal) (Doxil) | Ortho Biotech, Alza Corporation | Antineoplastic |
| Dronabinol (Marinol) | Unimed Pharmaceuticals, Inc. | Antiemetics |
| Entecavir (Baraclude) | Bristol-Myers Squibb | Antiviral |
| Epoetin alfa (Epogen, Procrit) | Ortho Biotech | Anemia |
| Etoposide (Etopophos (phosphate salt), Toposar, VePesid) | Pfizer, Bristol-Myers Squibb | Antineoplastic |
| Fluconazole (Diflucan) | Pfizer | Antifungal |
| Interferon alfa-2 (Intron A (2b), Roferon-A (2a) | Roche, Schering - 3 Plough | Biological response modifiers |
| Isoniazid (Nydrazid) | Sandoz, Hoffmann La-Roche | Antimycobacterial |
| Itraconazole (Sporanox) | Ortho Biotech, Janssen Pharmaceutica | Antifungal |
| Megestrol (Megace, Megace ES) | Bristol - Myers Squibb | Anticachectic |
| Paclitaxel (Onxol, Taxol) | Bristol - Myers Squibb, IVAX Pharmaceuticals | Antineoplastic |
| Peginterferon alfa-2 (PEG-Intron (2b), Pegasys (2a)) | Roche, Schering - Plough | Antiviral |
| Pentamidine (Nebupent) | American Pharmaceutical Partners, Fujisawa Health Care, Inc. | Antiprotozoal |
| Poly-L-lactic acid (Sculptra) | Dermik Laboratories | Dermal Filler |
| Rifabutin (Mycobutin) | Pharmacia Corporation | Antimycobacterial |
| Rifampin (Rifadin; Rimactane) | Aventis Pharmaceuticals | Antimycobacterial |
| Somatropin | Pharmacia Corporation, Serono Inc | Synthetic human growth hormone |
| Sulfamethoxazole/ Trimethoprim (Bactrim, Septra) (Serostim) | Alpha care Inc, Women First Health Care, King Pharmaceuticals | Antibacterial |
| Testosterone (Androderm, Androgel, Depo-Testosterone) | Pfizer Inc, Unimed Pharmaceuticals, Inc., Alza Corporation, Watson Laboratories | Androgens |
| Trimetrexate (Neutrexin) | United States Bioscience Inc, Medimmune, Inc. | Antiprotozoal |

The combinations of the compounds of this invention with AIDS antivirals, other antivirals, immunomodulators, anti-infectives, antibiotics, vaccines, other therapeutic agents are not limited to the list in the above Table, but includes, in principle, any combination with any pharmaceutical composition useful for the treatment against infection by HIV or for treating AIDS or ARC. Preferred combinations are simultaneous or alternating treatments of a compound of the present invention and a protease inhibitor (e.g., indinavir, nelfinavir, ritonavir, saquinavir and others), a reverse transcriptase inhibtor [nucleoside (e.g., AZT, 3TC, ddC, ddI, d4T, abacavir and others, are/or non-nucleoside (e.g., efavirenz, nevirapine, and others), or some combination of two or more of these inhibitors (see Table above). A few representative examples of relevant patents citing combinations are: EPO 0,484,071, U.S. Pat. No. 5,413,999, WO 9962513.

In such combinations the compound of the present invention and other active agents may be separately administered or concurrently administered. In addition, the administration of one element may be prior to, concurrent to, or subsequent to the administration of other agent(s).

The following representative examples are provided to illustrate details for the preparation of the compounds of the present invention. The examples are not intended to be limitations on the scope of the present invention and they should not be so construed. Furthermore, the compounds described in the following examples are not to be viewed as forming the only set of compounds that is considered as the invention, and any combination or components of the compounds of their moieties may itself form a set. This has been addressed previously in this patent document. Those skilled in the art will readily comprehend that known variations of reaction conditions and synthetic conversions described in the following preparative procedures can be used to prepare these other compounds.

Chemical Synthesis

REPRESENTATIVE EXAMPLE 1

4-(1,5-dibenzyl-1,2-dihydro-2-oxopyridin-3-yl)-2-hydroxy-4-oxobut-2-enoic acid (8)

The relevant scheme (1) is shown below.

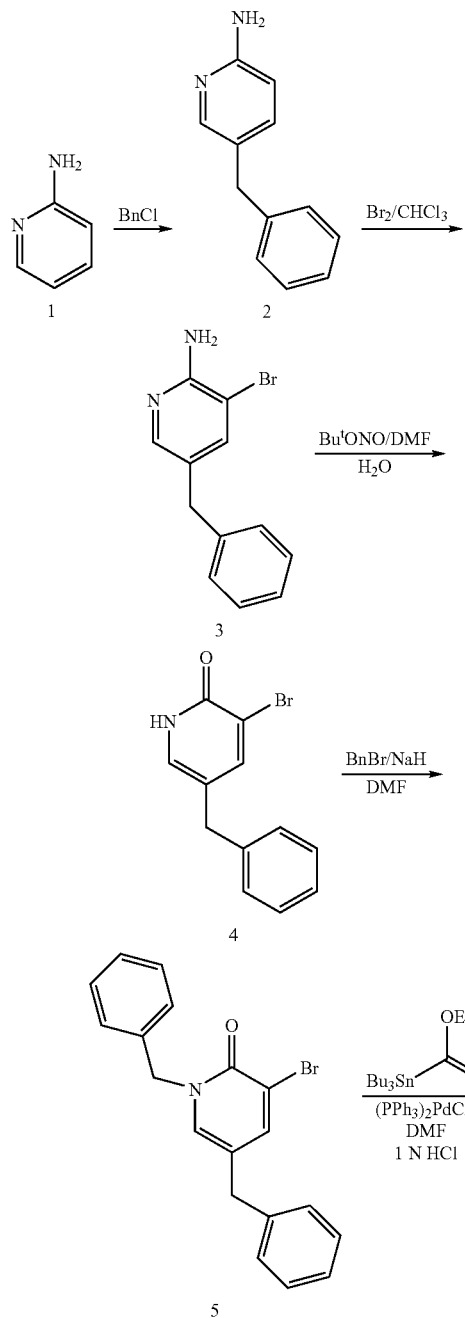

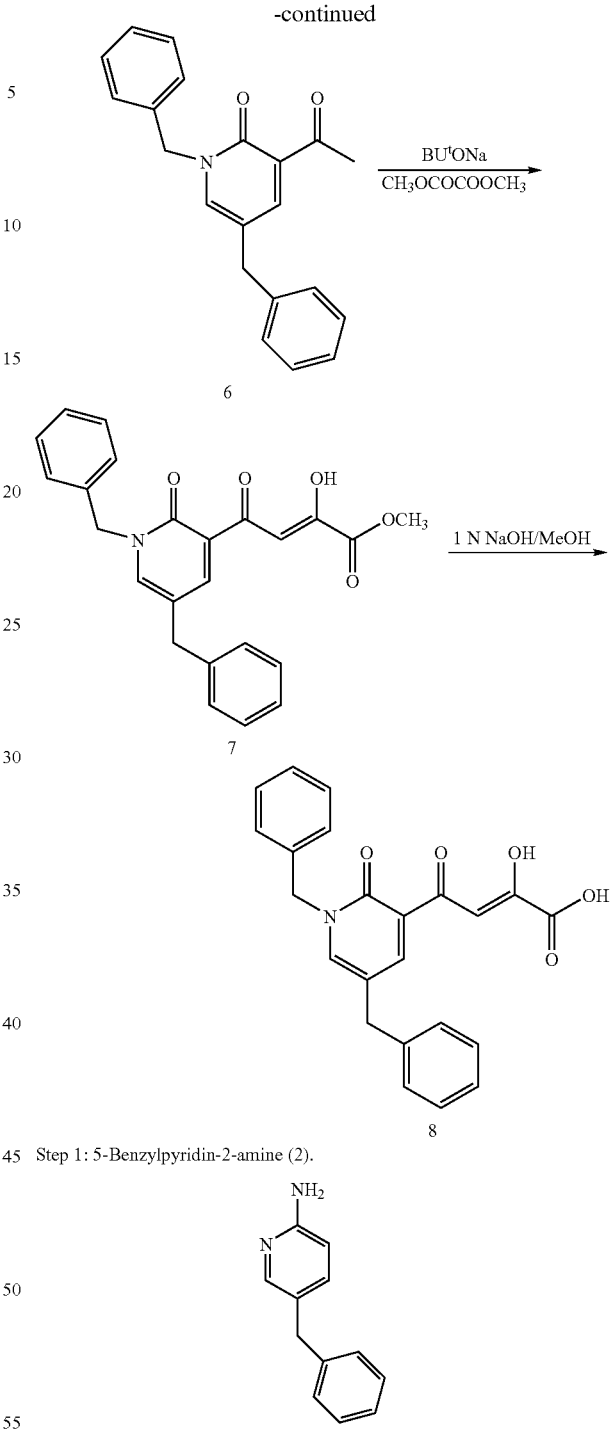

Step 1: 5-Benzylpyridin-2-amine (2).

A mixture of pyridine-2-amine 1 (14.1 g, 149.8 mmol) and benzylchloride (36.0 g, 284.6 mmol) was heated to 180° C. until the mixture began to boil [Kowalski, *J. Heterocycl. Chem.* 28, 875-879 (1991)]. The temperature was then gradually raised during 3 h to 250° C. and maintained for 24 h. After cooling, the reaction mixture was washed out from the flask with MeOH (60 mL) and treated with 10% aqueous $NH_4OH$ (40 mL). After addition of water (200 mL), the resulting oil was extracted with $CHCl_3$ (2×200 mL), dried over anhydrous $Na_2SO_4$, and $CHCl_3$ distilled off. The residue was separated by distillation under reduced pressure. The fraction collected at 130-135° C./1 mm Hg was further purified by flash chromatography on silica gel (EtOAc:hexane, 7:3). Yield 9.2 g (34%), white solid, mp 79-80° C. $^1$H NMR (CDCl$_3$, 500 MHz): δ 3.87 (s, 2H, CH$_2$), 4.43 (bs, 2H, NH$_2$), 6.48 (d, 1H, CH J=8.5 Hz), 7.19-7.33 (m, 6H, Ar—H and CH), 7.99 (d, 1H, CH, J=1.5 Hz). $^{13}$C NMR (CDCl$_3$, 125 MHz): δ 38.2, 108.7, 126.1, 126.4, 128.5, 128.7, 128.9, 128.9, 138.6, 140.9, 147.7, 156.8.

Step 2: 5-Benzyl-3-bromopyridin-2-amine (3)

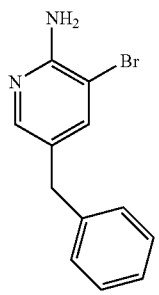

To a stirred solution of 5-benzylpyridin-2-amine 2 (6.0 g, 32.3 mmol) in CH$_2$C$_{12}$ (100 mL) cooled to 0° C. was added bromine (5.1 g, 32.3 mmol) dropwise [Kelly, et al., *J. Am. Chem. Soc.* 112, 8024-8034 (1990)]. The bromine decolorized immediately and the mixture was left stirring for 30 min. The mixture was shaken with saturated NaHCO$_3$ solution (100 mL), the organic layer was then dried over anhydrous Na$_2$SO$_4$, and distilled off to give a yellow residue which was purified by flash chromatography on silica gel (EtOAc: hexane, 3:7). Yield 7.3 g (86%), white solid, mp 110-111° C. $^1$H NMR (CDCl$_3$, 500 MHz): δ 3.86 (s, 2H, CH$_2$), 4.88 (bs, 2H, NH$_2$), 7.19-7.35 (m, 5H, Ar—H), 7.50 (d, 1H, CH, J=1.5 Hz), 7.94 (d, 1H, CH, J=1.0 Hz). $^{13}$C NMR (CDCl$_3$, 125 MHz): δ 37.7, 104.6, 126.4, 126.4, 128.1, 128.6, 128.6, 128.7, 140.2, 140.8, 146.7, 154.0; HRMS (M+H)$^+$ calcd for C$_{12}$H$_{13}$BrN$_2$ 263.0184, found 263.0184.

Step 3: 5-Benzyl-3-bromopyridin-2(1H)-one (4)

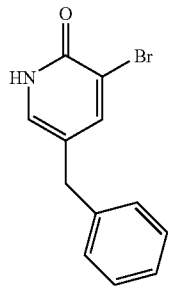

To a stirred solution of 5-benzyl-3-bromopyridin-2-amine 3 (0.2 g, 0.7 mmol) in DMF (4 mL) was added water (2 drops) followed by t-butyl nitrite (0.378 g, 3.6 mmol) and the reaction mixture stirred at RT for 30 min. DMF and the excess reagent were distilled off, and the residue purified by flash chromatography on silica gel (EtOAc:hexane, 1:1). Yield 7.3 g (86%), white solid, mp 151-152° C. $^1$H NMR (CDCl$_3$, 500 MHz): δ 3.77 (s, 2H, CH$_2$), 7.17-7.36 (m, 6H, Ar—H and CH), 7.76 (d, 1H, CH, J=1.5 Hz) 13.25 (bs, 1H, NH). $^{13}$C NMR (CDCl$_3$, 125 MHz): δ 37.3, 115.4, 121.0, 126.9, 128.8, 128.8, 128.9, 128.9, 132.4, 138.5, 145.3, 161.0; HRMS (M+H)$^+$ calcd for C$_{12}$H$_{11}$BrNO 264.0024, found 264.0014.

Step 4: 1,5-Dibenzyl-3-bromopyridin-2(1H)-one (5)

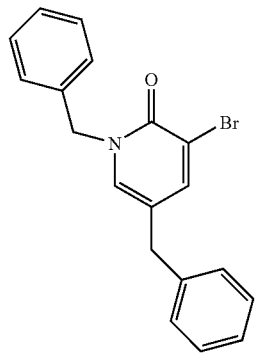

To a suspension of 5-benzyl-3-bromopyridin-2(1H)-one 4 (3.5 g, 13.5 mmol) in dry DMF (100 mL) was added NaH 60% suspension in mineral oil (0.5 g, 16.2 mmol) and stirred for 30 min, followed by the addition of benzyl bromide (0.1.36 g, 7.9 mmol) and mixture further stirred for 1 h at RT. DMF was distilled off and the residue redissolved in EtOAc (250 mL), washed with brine solution (2×100 mL), dried over anhydrous Na$_2$SO$_4$ and EtOAc distilled off to give a yellow syrup, which was purified by column chromatography on silica gel (EtOAc:Hexane, 4:6) to give 5. Yield 3.8 g (83%), yellow solid, mp 89-90° C. $^1$H NMR (CDCl$_3$, 500 MHz): δ 3.69 (s, 2H, CH$_2$), 5.18 (s, 2H, CH$_2$), 7.11 (d, 1H, CH, J=2 Hz), 7.12-7.39 (m, 10H, Ar—H), 7.60 (d, 1H, CH, J=2 Hz), $^{13}$C NMR (CDCl$_3$, 125 MHz): δ 37.4, 53.5, 117.1, 119.1, 126.9, 128.2, 128.2, 128.3, 128.3, 128.6, 128.8, 128.8, 128.9, 128.9, 134.6, 135.8, 138.7, 143.0, 158.3. HRMS (M+H)$^+$ calcd for C$_{19}$H$_{17}$BrNO 354.0494, found 354.0455.

Step 5: 3-Acetyl-1,5-dibenzyl-3-pyridin-2(1H)-one (6)

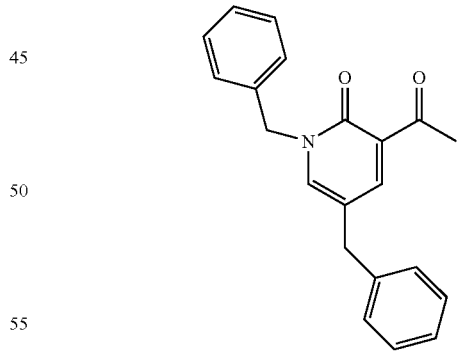

A mixture of 1,5-dibenzyl-3-bromopyridin-2(1H)-one 5 (1.0 g, 2.8 mmol) bis(triphenylphosphine)palladium(II) chloride (0.19 g, 0.28 mmol) and ethoxyvinyl(tributyl)tin (2.03 g, 5.6 mmol) in dry DMF (50 mL) was heated under N$_2$ at 70° C. for 1 h. DMF was distilled off and the resulting residue redissolved in EtOAc (50 mL) and filtered through a pad of celite. EtOAc fraction was stirred with 1 N HCl (30 mL) for 15 min, washed with water (2×30 mL), and dried over anhydrous Na$_2$SO$_4$ and distilled off to give a yellow residue which was purified by flash chromatography on silica gel (EtOAc: hexane, 2:8). Yield 0.86 g (97%), yellow oil. $^1$H NMR (CDCl$_3$, 500 MHz): δ 2.73 (s, 3H, CH$_3$), 3.75 (s, 2H, CH$_2$), 5.19 (s, 2H, CH$_2$), 7.14-7.40 (m, 11H, Ar—H and CH), 8.04 (d, 1H, CH, J=3 Hz). $^{13}$C NMR (CDCl$_3$, 125 MHz): δ 31.1, 37.5, 52.5, 118.6, 126.8, 127.8, 127.8, 127.9, 128.2, 128.2, 128.6, 128.6, 128.8, 128.8, 129.0, 135.8, 138.8, 140.7, 144.8, 160.4, 198.0; HRMS (M+H)$^+$ calcd for C$_{21}$H$_{20}$NO$_2$ 318.1494, found 318.1461.

Step 6: Methyl-4-(1,5-dibenzyl-1,2-dihydro-2-oxopyridin-3-yl)-2-hydroxy-4-oxobut-2-enoate (7)

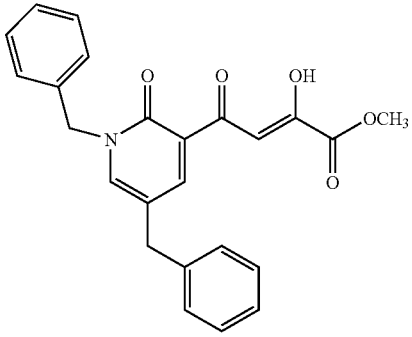

To a stirred solution of 3-acetyl-1,5-dibenzyl-3-pyridin-2 (1H)-one 6 (0.1 g, 0.31 mmol) in THF (5 mL) was added Na-t-butoxide (0.30 g, 3.1 mmol) and the reaction mixture stirred for 15 min. A solution of dimethyl oxalate (0.37 g, 3.1 mmol) in THF (5 mL) was added at RT and stirred for 2 h. THF was distilled off and 1 N HCl (1 mL) was added and extracted with EtOAc (2×10 mL), washed with saturated brine solution (4×20 mL), dried over anhydrous sodium sulfate and EtOAc distilled off to give a brown residue which was purified first by ion exchange chromatography (Diethylamino sephadex anion exchange resin, (CH$_3$CN:H$_2$O, 1:1) and then by flash chromatography on silica gel (CHCl$_3$:MeOH, 9.9: 0.1). Yield 0.054 g (44%), yellow oil. $^1$H NMR (CDCl$_3$, 500 MHz): δ 3.79 (s, 2H, CH$_2$), 3.91 (s, 3H, CH$_3$), 5.21 (s, 2H, CH$_2$), 7.15-7.42 (m, 11H, Ar—H and CH), 7.98 (s, 1H, olefenic CH), 8.24 (d, 1H, CH, J=2.5 Hz), $^{13}$C NMR (CDCl$_3$, 100 MHz): δ 37.5, 52.7, 53.0, 101.8, 119.0, 123.4, 126.9, 128.0, 128.0, 128.3, 128.6, 128.6, 128.9, 129.0, 129.0, 129.1, 135.6, 138.6, 141.4, 145.0, 159.5, 162.6, 172.2, 185.5; HRMS (M+H)$^+$ calcd for C$_{24}$H$_{22}$NO$_5$ 404.1498, found 404.1411.

Step 7: 4-(1,5-Dibenzyl-1,2-dihydro-2-oxopyridin-3-yl)-2-hydroxy-4-oxobut-2-enoic acid (8)

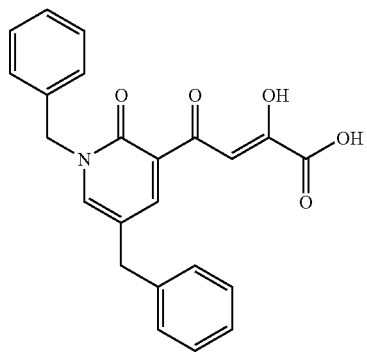

To a stirred solution of methyl-4-(1,5-dibenzyl-1,2-dihydro-2-oxopyridin-3-yl)-2-hydroxy-4-oxobut-2-enoate 7 (0.069 g, 0.17 mmol) in MeOH (5 mL) at 0° C. was added a solution of 1N NaOH (0.5 mL) and reaction mixture allowed to stir at 0° C. for 30 min. Reaction was then allowed to stir at ambient temperature for 1 h. The reaction mixture was neutralized with 1 N HCl, the solid separated was filtered and dried under vacuum. Recrystallization with EtOAc/Hexane gave yellow solid. Yield 0.034 g (52%), yellow solid, mp 158-159° C. $^1$H NMR (CDCl$_3$, 500 MHz): δ 3.82 (s, 2H, CH$_2$), 5.26 (s, 2H, CH$_2$), 7.16-7.39 (m, 10H, Ar—H), 7.45 (d, 1H, CH, J=2 Hz), 7.98 (s, 1H, olefenic CH), 8.26 (d, 1H, CH, J=2 Hz), $^{13}$C NMR (CDCl$_3$, 125 MHz): δ 37.5, 53.3, 100.8, 119.8, 123.1, 127.0, 128.2, 128.5, 128.5, 128.6, 128.6, 128.9, 128.9, 129.0, 129.1, 129.1, 135.2, 138.4, 141.3, 145.1, 159.5, 162.3, 173.7; HRMS (M+H)$^+$ calcd for C$_{23}$H$_{20}$NO$_5$ 390.1341, found 390.1342.

REPRESENTATIVE EXAMPLE 2

4-(1,5-dibenzyl-1,4-dihydro-4-oxopyridin-3-yl)-2-hydroxy-4-oxobut-2-enoic acid (16)

The relevant scheme (2) is shown below.

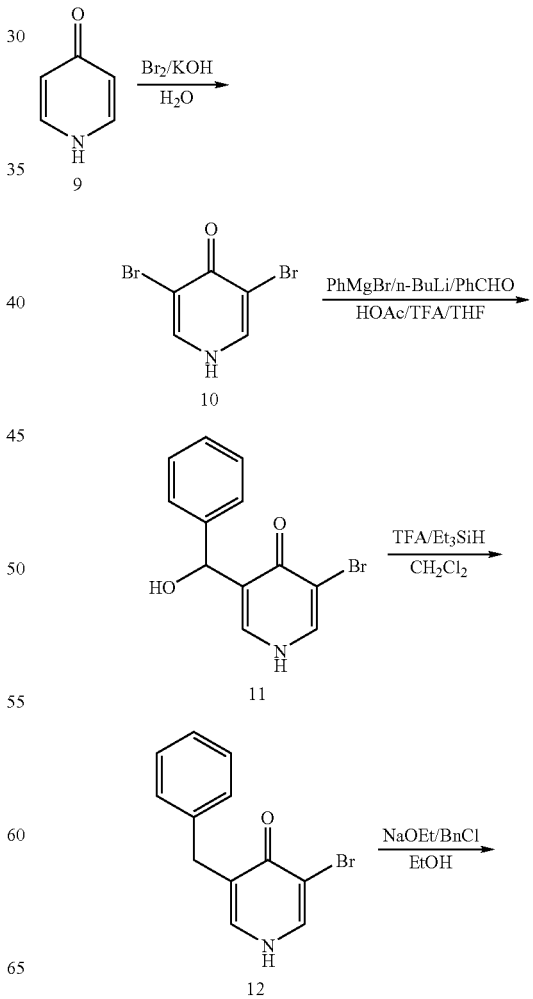

Scheme 2

-continued

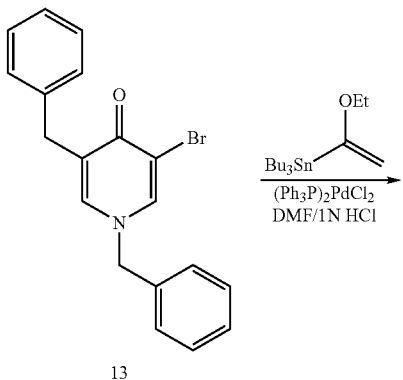

13

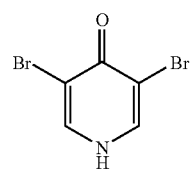

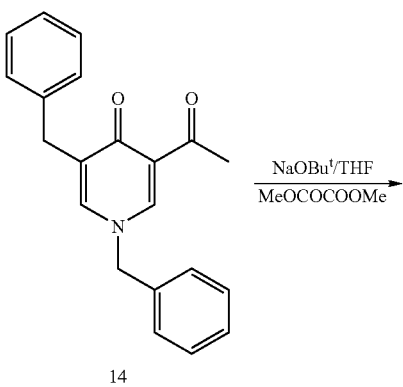

14

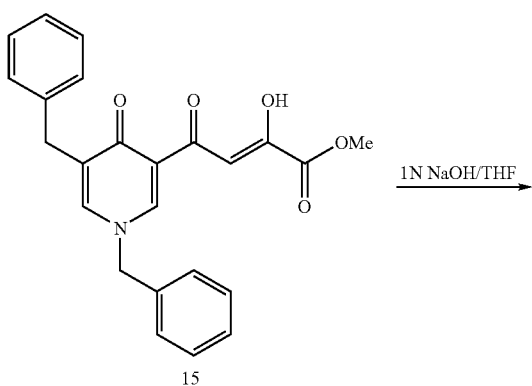

15

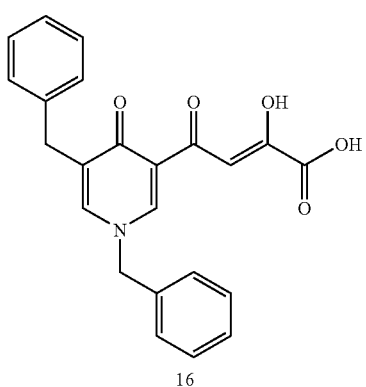

16

Step 1: 3,5-Dibromo-pyridin-4-one (10)

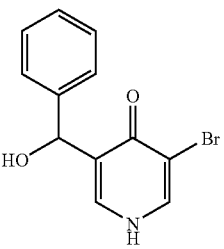

To an ice-cooled solution of pyridine-4-one 9 (6.98 g, 73.4 mmol) and KOH (9.52 g, 146.8 mmol) in water (140 mL) was added bromine (7.58 mL, 147.5 mmol) dropwise over 30 min [Spivey, et al., *J. Org. Chem.* 65, 3154-3159 (2000)]. After an additional 30 min, the precipitate was filtered off, washed with a copious amount of water, and dried in vacuo. Yield 16.17 g (87%), yellow solid, mp 320° C. (sublimes). $^1$H NMR (DMSO-$d_6$, 500 MHz): δ 12.3 (s, 1H), 8.26 (s, 2H). $^{13}$C NMR (DMSO-$d_6$, 125 MHz): δ 167.5, 138.2, 138.2, 111.8, 111.8.

Step 2: 3-Bromo-5-(hydroxy-phenyl-methyl)-pyridin-4-one (11)

To a heterogeneous mixture of 3,5-dibromo-pyridin-4-one 10 (0.313 g, 1.24 mmol) in anhydrous THF (4 mL) at −78° C. under nitrogen atmosphere was added phenylmagnesium bromide solution (1.36 mL of 1 M solution in THF, 1.36 mmol) [Borzilleri, et al., U.S. Pat. 20050245530]. After stirring for 15 min, n-BuLi solution (0.68 mL of 2 M solution in cyclohexane, 1.36 mmol) was added and the reaction mixture stirred for 15 min at −78° C. under nitrogen atmosphere. To this mixture was added benzaldehyde (0.26 mL, 2.6 mmol) and the mixture was stirred for 2 h at −78° C. The reaction mixture was quenched by adding HOAc (0.38 mL) and TFA (0.38 mL), concentrated in vacuo and the residue was purified by flash column chromatography on silica gel (dichloromethane:methanol, 95:5). Yield 0.125 g (36%), white solid, 123-124° C. $^1$H NMR (MeOH—$d_4$, 500 MHz): δ 8.09 (s, 1H), 7.81 (s, 1H), 7.38-7.17 (m, 5H), 5.92 (s, 1H), 3.83 (s, 2H). $^{13}$C NMR (MeOH—$d_4$, 125 MHz): δ 174.3, 144.4, 139.7, 135.8, 133.6, 129.4, 129.3, 128.6, 128.0, 128.0, 114.8, 70.8.

Step 3: 3-Benzyl-5-bromopyridin-4-one (12)

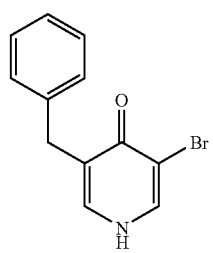

A mixture of 3-bromo-5-(hydroxyl-phenyl-methyl)pyridin-4-one 11 (0.125 g, 91 mmol), TFA (16 mL) and Et₃SiH in anhydrous dichloromethane (30 mL) was stirred at rt for 10 h [Borzilleri, et al., U.S. Pat. 20050245530]. The reaction mixture was concentrated in vacuo and the residue purified by flash column chromatography on silica gel (dichloromethane:methanol, 98:2). Yield 0.081 g (69%), white solid. $^1$H NMR (MeOH—d$_4$, 500 MHz): δ 8.12 (s, 1H), 7.47 (s, 1H), 7.29-7.17 (m, 5H), 3.83 (s, 2H). $^{13}$C NMR (MeOH—d$_4$, 125 MHz): δ 175.2, 140.7, 139.5, 136.9, 130.8, 130.0, 130.0, 129.5, 129.5, 127.3, 114.1, 34.9.

Step 4: 1,3-Dibenzyl-5-bromo-1H-pyridin-4-one (13)

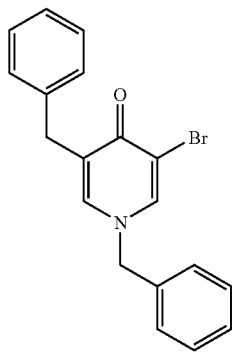

A mixture of 3-benzyl-5-bromopyridin-4-one 12 (0.57 g, 2.16 mmol) and NaOEt (0.89 mL, 2.37 mmol) in absolute ethanol (20 mL) was refluxed with benzyl chloride (0.30 mL, 2.59 mmol) for 1 h under nitrogen. The solvent was distilled off to give a yellow residue which was purified by flash column chromatography on silica gel (dichloromethane:methanol, 98:2). Yield 1.31 g (96.7%), yellow solid, mp 120-121° C. $^1$H NMR (CDCl₃, 500 MHz): δ 7.67 (d, 1H, J=2.4), 7.32-7.07 (m, 10H), 4.83 (s, 1H), 3.78 (s, 2H). $^{13}$C NMR (CDCl₃, 125 MHz): δ 172.2, 139.6, 139.1, 137.6, 134.7, 129.9, 129.9, 129.3, 129.3, 129.2, 129.0, 128.6, 128.6, 127.5, 127.6, 126.4, 114.1, 60.3, 34.4. HRMS (M+H)⁺ calcd for C₁₉H₁₆BrNO 354.0494, found 354.0499.

Step 5: 3-Acetyl-1,5-dibenzyl-1H-pyridin-4-one (14)

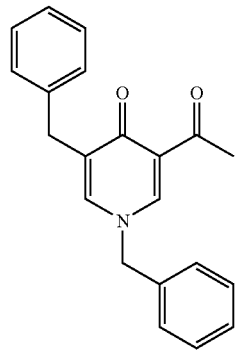

A mixture of 1,3-dibenzyl-5-bromo-1H-pyridin-4-one 13 (1.31 g, 2.70 mmol), tributyl-(1-ethoxyvinyl)tin (1.80 mL, 5.18 mmol) and dichlorobis(triphenylphosphine)-palladium (II) (0.26 g, 0.37 mmol) in anhydrous DMF (20 mL) was stirred under nitrogen atmosphere at 95° C. for 8 h. The reaction mixture was extracted with ethyl acetate (3×50 mL), washed with 1N HCl (3×50 mL), and solvent distilled off. The residue was purified by flash column chromatography on silica gel (dichloromethane:methanol, 98:2). Yield 1.06 g (90%), yellow oil. $^1$H NMR (CDCl₃, 500 MHz): δ 8.19 (d, 1H, J=2.6), 7.39-7.10 (m, 10H), 6.90 (d, 1H, J=2.5), 4.89 (s, 2H), 3.81 (s, 2H), 2.74 (s, 3H). HRMS (M+H)⁺ calcd for C₂₁H₁₉NO₂ 318.1494, found 318.1493.

Step 6: Methyl 4-(1,5-dibenzyl-4-oxo-1,4-dihydropyridin-3-yl)-2-hydroxy-4-oxo-but-2-enoate (15)

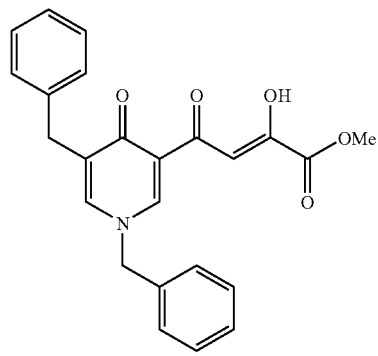

To a stirred solution of sodium t-butoxide (0.52 g, 5.23 mmol) in anhydrous THF (13 mL) at room temperature was added dropwise dimethyl oxalate (0.42 g, 3.48 mmol) in THF (6 mL) followed by 3-acetyl-1,5-dibenzyl-1H-pyridin-4-one 14 (0.55 g, 1.74 mmol) in THF (8 mL). The resulting mixture was stirred at room temperature for 4 h and then acidified (pH=6). The crude product was extracted with ethyl acetate (100 mL), washed with water (2×100 mL) and brine (2×100 mL), and dried over anhydrous sodium sulfate and the solvent was distilled off. The residue was purified by ion exchange chromatography (diethylamino sephadex anion exchange resin (CH₃CN:H₂O, 1:1) and then by flash chromatography on silica gel (chloroform, 100%). Yield 0.44 g (63%), mp 148-150° C. $^1$H NMR (CDCl$_3$, 500 MHz): δ 8.34 (d, J=2.5, 1H), 8.12 (s, 1H), 7.40-7.12 (m, 10H), 6.91 (d, J=2.3, 1H), 4.94 (s, 2H), 3.88 (s, 3H), 3.82 (s, 2H). $^{13}$C NMR (CDCl$_3$, 125 MHz): δ 187.2, 175.2, 170.3, 162.7, 143.9, 138.4, 136.9, 136.1, 133.8, 129.4, 129.5, 129.3, 129.1, 129.1, 128.7, 128.6, 127.5, 127.4, 126.5, 120.2, 102.4, 61.2, 53.0, 33.5. HRMS (M+H)$^+$ calcd for C$_{24}$H$_{22}$NO$_5$ 404.1498, found 404.1497.

Step 7: 4-(1,5-dibenzyl-1,4-dihydro-4-oxopyridin-3-yl)-2-hydroxy-4-oxobut-2-enoic acid (16)

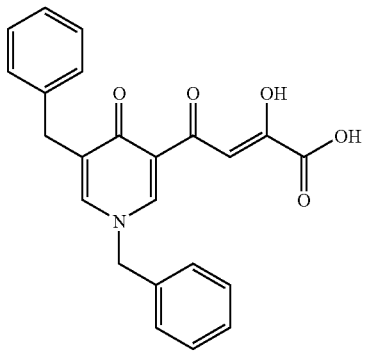

A mixture of methyl-4-(1,5-dibenzyl-1,4-dihydro-4-oxopyridin-3-yl)-2-hydroxy-4-oxobut-2-enoate 15, (0.080 g, 0.19 mmol) and 1 N NaOH (4 mL) in THF (12 mL) was stirred at 0° C. for 4 h. THF was distilled off and the residue acidified with 1 N HCl and extracted with EtOAc (2×25 mL), washed with brine solution (1×25 mL), dried over anhydrous Na$_2$SO$_4$ and EtOAc distilled off to give a yellow solid. The crude solid was triturated with diethylether, filtered and dried under vacuum. Finally the solid was triturated with chloroform, filtered and dried under vacuum for 24 h. Yield 0.065 g (84%), yellow solid, mp 140-142° C. $^1$H NMR (CDCl$_3$+MeOH-d$_4$, 500 MHz): δ 3.80 (s, 2H, CH$_2$), 4.97 (s, 2H, CH$_2$), 6.95 (t, 1H, CH, J=1 Hz), 7.13-7.40 (m, 11H, Ar—H and olefenic CH), 8.36 (d, 1H, CH, J=2.5 Hz). $^{13}$C NMR (CDCl$_3$, 125 MHz): δ 33.4, 61.2, 120.5, 126.5, 127.5, 127.6, 128.6, 128.7, 128.7, 129.1, 129.1, 129.2, 129.2, 129.2, 129.4, 133.8, 135.9, 137.2, 138.2, 143.8, 163.8, 175.4. HRMS (M+H)$^+$ calcd for C$_{23}$H$_{20}$NO$_5$ 390.1341, found 390.1343.

We claim:

1. A compound according to the structure of formula I:

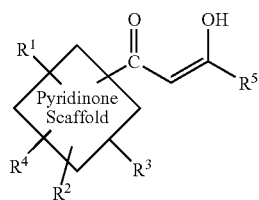

wherein the scaffold is independently the 2- and 4-pyridinones identified herein and their regioisomers;

R$^1$ and R$^2$ are each independently H, C$_{1-6}$ alkyl, C$_{1-6}$ fluoroalkyl, unsubstituted or substituted C$_{5-6}$ cycloalkyl, C$_{1-6}$ alkenyl, unsubstituted or substituted phenyl, unsubstituted or substituted benzyl, C$_{2-6}$ alkyl phenyl which phenyl moiety may be optionally substituted, unsubstituted or substituted heteroaryl, C$_{1-6}$ alkyl substituted with a heteroaryl group which heteroaryl group is optionally substituted, C$_{1-6}$ alkyl S(O)R or alkyl (SO$_2$)R where R is alkyl, phenyl or substituted phenyl, C$_{1-6}$ alkyl CO$_2$R$^a$ where R$^a$ is C$_{1-6}$ alkyl or H, C$_{1-6}$ alkyl COR$^{a'}$ where R$^{a-}$ is C$_{1-6}$ alkyl;

R$^3$ and R$^4$ are independently selected from H, C$_{1-6}$ alkyl, halogen, hydroxyl, unsubstituted or substituted benzyl, or unsubstituted or substituted phenylthio;

R$^5$ is CO$_2$R$^c$ or P(O)(OR$^c$)(OR$^c$), where each R$^c$ is independently from H and C$_{1-6}$ alkyl, Or a pharmaceutically acceptable salt thereof.

2. A compound of claim 1 according to the structure:

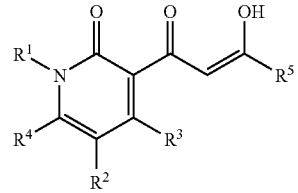

wherein R$^1$ and R$^2$ are each independently a benzyl group or a substituted benzyl group with 1 to 3 substituents on the aromatic ring selected from halogen, hydroxyl, methoxy, methyl, ethyl, propyl, CF$_3$ or a —CH$_2$R$^b$ group where R$^b$ is a 5- or 6-membered heteroaryl group;

R$^3$ and R$^4$ are independently H, C$_{1-6}$ alkyl, halogen, benzyl, substituted benzyl, phenylthio, or substituted phenylthio with 1 to 3 substitutents on the phenyl ring selected from halogen, hydroxyl, methoxy, methyl, ethyl, propyl, CF$_3$;

wherein R$^5$ is CO$_2$R where R is selected from H and C$_{1-6}$ alkyl, or a pharmaceutically acceptable salt thereof.

3. The compound of claim 1 according to the structure:

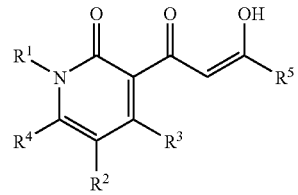

wherein R$^1$ and R$^2$ are each independently a benzyl group or substituted benzyl group with 1 to 3 substituents on the aromatic ring selected from halogen, hydroxyl, methoxy, methyl, ethyl, propyl, CF$_3$ or wherein R$^1$ and R$^2$ are independently —CH$_2$R$^b$ where R$^b$ is a 5- or 6-membered heteroaromatic ring;

wherein R$^3$ and R$^4$ are independently H, C$_{1-6}$ alkyl, halogen, benzyl, substituted benzyl, phenylthio, or substituted phenylthio with 1 to 3 substitutents on the phenyl ring selected from halogen, methoxy, methyl, ethyl, propyl, CF$_3$;

wherein R$^5$ is P(O)(OR)(OR), where the R groups could be the same or not and are selected from H or C$_{1-6}$ alkyl, or a pharmaceutically acceptable salt thereof.

4. A compound of claim 1 according to the structure:

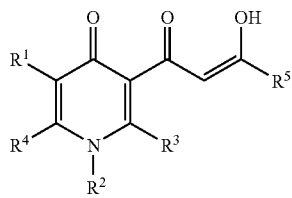

wherein $R^1$ and $R^2$ are each independently a benzyl group or a substituted benzyl group with 1 to 3 substituents on the aromatic ring selected from halogen, hydroxyl, methoxy, methyl, ethyl, propyl, $CF_3$ or a —$CH_2R^b$ group where $R^b$ is a 5- or 6-membered heteroaryl group;
$R^3$ and $R^4$ are independently H, $C_{1-6}$ alkyl, halogen, benzyl, substituted benzyl, phenylthio, or substituted phenylthio with 1 to 3 substitutents on the phenyl ring selected from halogen, hydroxyl, methoxy, methyl, ethyl, propyl, $CF_3$:
wherein $R^5$ is $CO_2R$ where R is selected from H and $C_{1-6}$ alkyl,
or a pharmaceutically acceptable salt thereof.

5. A compound of claim 1 according to the structure:

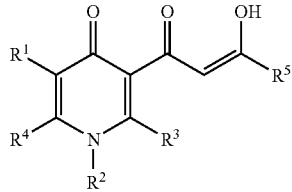

wherein $R^1$ and $R^2$ are each independently a benzyl group or substituted benzyl group with 1 to 3 substituents on the aromatic ring selected from halogen, hydroxyl, methoxy, methyl, ethyl, propyl, $CF_3$ or wherein $R^1$ and $R^2$ are independently —$CH_2R^b$ where $R^b$ is a 5- or 6-membered heteroaromatic ring;
wherein $R^3$ and $R^4$ are independently H, $C_{1-6}$ alkyl, halogen, benzyl, substituted benzyl, phenylthio, or substituted phenylthio with 1 to 3 substitutents on the phenyl ring selected from halogen, methoxy, methyl, ethyl, propyl, $CF_3$:
wherein $R^5$ is $P(O)(OR)(OR)$, where the R groups could be the same or not and are selected from H or alkyl,
or a pharmaceutically acceptable salt thereof.

6. A compound selected from the group consisting of
4-(1,5-dibenzyl-1,2-dihydro-2-oxopyridin-3-yl)-2-hydroxy-4-oxobut-2-enoic acid;
4-(1,5-dibenzyl-1,4-dihydro-4-oxopyridin-3-yl)-2-hydroxy-4-oxobut-2-enoic acid;
3-Acetyl-1,5-dibenzyl-3-pyridin-2(1H)-one;
3-Acetyl-1,5-dibenzyl-1H-pyridin-4-one;
Methyl-4-(1,5-dibenzyl-1,2-dihydro-2-oxopyridin-3-yl)-2-hydroxy-4-oxobut-2-enoate; and
Methyl 4-(1,5-dibenzyl-4-oxo-1,4-dihydro-pyridin-3-yl)-2-hydroxy-4-oxo-but-2-enoate, or a pharmaceutically acceptable salt thereof.

7. The compound
4(1,5-dibenzyl-1,2-dihydro-2-oxopyridin-3-yl)-2-hydroxy-4-oxobut-2-enoic acid;
4-(1,5-dibenzyl-1,4-dihydro-4-oxopyridin-3-yl)-2-hydroxy-4-oxobut-2-enoic acid, or
a pharmaceutically acceptable salt thereof.

8. A compound of claim 1 according to the structure:

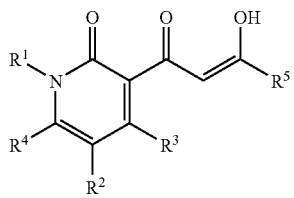

wherein $R^1$ and $R^2$ are independently benzyl groups or substituted benzyl groups with 1 to 3 substituents on the phenyl rings selected from the group consisting of fluorine, chlorine, $C_{1-4}$ alkyl, $C_{2-4}$ alkenyl and methoxy;
$R^3$ is H, $C_{1-3}$ alkyl, $C_{2-3}$ alkenyl, fluorine, chlorine or methoxy;
$R^4$ is H, F, Cl or OH; and
$R^5$ is $CO_2H$ or $P(O)(OH)_2$,
or, a pharmaceutically acceptable salt thereof.

9. The compound according to claim 1 wherein at least one of $R^1$ and $R^2$ is a benzyl group.

10. The compound according to claim 1 wherein both $R^1$ and $R^2$ are benzyl groups.

11. The compound according to claim 8 wherein both $R^1$ and $R^2$ are benzyl groups.

12. The compound according to claim 1 wherein $R^3$ and $R^4$ are independently H, methyl, fluorine or chlorine.

13. The compound according to claim 9 wherein $R^3$ and $R^4$ are independently H, methyl, fluorine or chlorine.

14. The compound according to claim 10 wherein $R^3$ and $R^4$ are independently H, methyl, fluorine or chlorine.

15. The compound according to claim 11 wherein $R^3$ and $R^4$ are independently H, methyl, fluorine or chlorine.

16. The compound according to claim 1 wherein $R^3$ and $R^4$ are independently H, fluorine or chlorine.

17. The compound according to claim 8 wherein $R^3$ and $R^4$ are independently H, fluorine or chlorine.

18. The compound according to claim 1 wherein $R^3$ and $R^4$ are each H.

19. The compound according to claim 8 wherein $R^3$ and $R^4$ are each H.

20. The compound according to claim 12 wherein $R^3$ and $R^4$ are each H.

21. The compound according to claim 1 wherein $R^5$ is $CO_2H$ or a pharmaceutically acceptable salt thereof.

22. The compound according to claim 8 wherein $R^5$ is $CO_2H$ or a pharmaceutically acceptable salt thereof.

23. The compound according to claim 9 wherein $R^5$ is $CO_2H$ or a pharmaceutically acceptable salt thereof.

24. The compound according to claim 10 wherein $R^5$ is $CO_2H$ or a pharmaceutically acceptable salt thereof.

25. The compound according to claim 11 wherein $R^5$ is $CO_2H$ or a pharmaceutically acceptable salt thereof.

26. The compound according to claim 12 wherein $R^5$ is $CO_2H$ or a pharmaceutically acceptable salt thereof.

27. The compound according to claim 13 wherein $R^5$ is $CO_2H$ or a pharmaceutically acceptable salt thereof.

28. The compound according to claim 14 wherein $R^5$ is $CO_2H$ or a pharmaceutically acceptable salt thereof.

29. A pharmaceutical composition comprising a therapeutically effective amount of a compound according to claim 1 and a pharmaceutically acceptable carrier, additive or excipient.

30. The pharmaceutical composition of claim 29 wherein said composition inhibits HIV integrase, both wild type and mutants, in a human host.

31. A pharmaceutical composition comprising a therapeutically effective amount of a compound according to claim 1 in combination with a therapeutically effective amount of at least one compound selected from the group consisting of i) an additional anti-HIV agent, ii) an anti-infective agent other than an anti-HIV agent, iii) an immunomodulator, iv) other combination agent selected from the table shown on pages 16-27, herein, and a pharmaceutically acceptable carrier, additive or excipient.

32. The composition according to claim 31 wherein said anti-infective agent is an antiviral agent selected from the group consisting of a protease inhibitor, a reverse transcriptase inhibitor, an additional integrase inhibitor or a combination thereof.

33. The composition of claim 32 wherein said reverse transcriptase inhibitor is a nucleoside compound.

34. The composition of claim 32 wherein said reverse transcriptase inhibitor is a non-nucleoside compound.

35. The composition of claim 32 wherein the said additional integrase inhibitor is a compound other than a pyrimidinone compound.

36. The composition of claim 29 in oral or parenteral dosage form.

37. The composition of claim 30 in oral or parenteral dosage form.

38. The composition according to claim 29 formulated for administration as an inhalation spray or a rectal suppository.

39. The composition according to claim 30 formulated for administration as an inhalation spray or a rectal suppository.

40. A method of preparing a pharmaceutical composition comprising combining a compound of claim 1 with a pharmaceutically-acceptable carrier, additive or excipient to produce a mixture and preparing an oral or parenteral dosage form from said mixture.

41. A method of treating an HIV infection in a patient, said method comprising administering to said patient an effective amount of a composition according to claim 29 to said patient.

42. A method of treating an HIV infection in a patient, said method comprising administering to said patient an effective amount of a composition according to claim 30 to said patient.

43. A method of reducing the likelihood of an HIV infection in a patient at risk for said infection, said method comprising administering to said patient an effective amount of a composition according to claim 29 to said patient.

44. A method of reducing the likelihood of an HIV infection in a patient at risk for said infection, said method comprising administering to said patient an, effective amount of a composition according to claim 30 to said patient.

45. A method of treating a patient with AIDS or ARC comprising administering to said patient a therapeutically effective amount of the composition according to claim 29.

46. A method of treating a patient with AIDS or ARC comprising administering to said patient a therapeutically effective amount of the composition according to claim 30.

47. A method of inhibiting HIV integrase in a subject, said method comprising administering to said subject a therapeutically effective amount of a compound according to any of claims 1-28 to said subject.

48. The method of claim 47 wherein said subject is a human.

* * * * *